United States Patent
Stefl et al.

(10) Patent No.: US 12,285,532 B2
(45) Date of Patent: Apr. 29, 2025

(54) SYSTEMS AND METHODS TO DISINFECT AN OBJECT OR SURFACE

(71) Applicant: Illinois Tool Works Inc., Glenview, IL (US)

(72) Inventors: Barbara Ann Stefl, Lebanon, OH (US); William Richard Immell, Liberty Township, OH (US); William Mark Feldmann, Cincinnati, OH (US); Jeem Newland, III, Springboro, OH (US)

(73) Assignee: Illinois Tool Works Inc., Glenview, IL (US)

(*) Notice: Subject to any disclaimer, the term of this patent is extended or adjusted under 35 U.S.C. 154(b) by 763 days.

(21) Appl. No.: 17/573,879

(22) Filed: Jan. 12, 2022

(65) Prior Publication Data

US 2022/0218853 A1 Jul. 14, 2022

Related U.S. Application Data

(60) Provisional application No. 63/137,337, filed on Jan. 14, 2021.

(51) Int. Cl.
*A61L 2/10* (2006.01)
*A61L 2/14* (2006.01)
(Continued)

(52) U.S. Cl.
CPC .......... *A61L 2/10* (2013.01); *A61L 2/14* (2013.01); *A61L 2/208* (2013.01); *A61L 2/26* (2013.01);
(Continued)

(58) Field of Classification Search
CPC ..... A61L 2/00; A61L 2/08; A61L 2/10; A61L 2/14; A61L 2/20; A61L 2/208;
(Continued)

(56) References Cited

U.S. PATENT DOCUMENTS

| 4,309,388 A | 1/1982 | Tenney |
| 7,397,041 B1 * | 7/2008 | Leonard .................. A61L 2/10 |
| | | 250/455.11 |

(Continued)

OTHER PUBLICATIONS

JP 2004275330 A with machine translation of Abstract (Year: 2004).*

(Continued)

*Primary Examiner* — Natasha E Young
(74) *Attorney, Agent, or Firm* — McAndrews, Held & Malloy, Ltd.

(57) ABSTRACT

Systems and methods for treating an object, in particular, for disinfecting and/or drying objects and/or surfaces are provided. One or more of an air delivery system, an electromagnetic emitter (e.g., a Far ultraviolet (UV) light source), and/or an air treatment device (e.g., a gaseous hydrogen-peroxide generator) may be used to condition ambient air to treat a surface or container for use (e.g., prior to filling the container, applying a surfactant, etc.). An ionizer may be employed with one or more of the emitter or air treatment device to additionally remove static from air within or provided to a treatment area.

20 Claims, 5 Drawing Sheets

(51) Int. Cl.
*A61L 2/20* (2006.01)
*A61L 2/26* (2006.01)
*B08B 9/093* (2006.01)
*F26B 15/18* (2006.01)
*F26B 21/00* (2006.01)

(52) U.S. Cl.
CPC ............ *B08B 9/093* (2013.01); *F26B 21/004* (2013.01); *A61L 2202/11* (2013.01); *A61L 2202/122* (2013.01); *A61L 2202/17* (2013.01); *B08B 2209/08* (2013.01); *F26B 15/18* (2013.01)

(58) Field of Classification Search
CPC .... A61L 2/26; A61L 2202/00; A61L 2202/10; A61L 2202/11; A61L 2202/12; A61L 2202/122; A61L 2202/17; B08B 9/00; B08B 9/08; B08B 9/093; B08B 2209/00; B08B 2209/08; F26B 15/00; F26B 15/10; F26B 15/12; F26B 15/18; F26B 21/00; F26B 21/004

See application file for complete search history.

(56) References Cited

U.S. PATENT DOCUMENTS

2019/0255201 A1* 8/2019 Rosen .................. A61L 2/0052
2020/0360551 A1 11/2020 Naito

OTHER PUBLICATIONS

Int'l Search Report and Written Opinion Appln No. PCT/US2022/012232 mailed May 3, 2022.

* cited by examiner

SYSTEMS AND METHODS TO DISINFECT AN OBJECT OR SURFACE

CROSS-REFERENCE TO RELATED APPLICATIONS

This application hereby claims priority to and the benefit of U.S. Provisional Application Ser. No. 63/137,337, entitled "Systems And Methods To Disinfect An Object Or Surface," filed Jan. 14, 2021. U.S. Provisional Application Ser. No. 63/137,337 is hereby incorporated by reference in its entireties for all purposes.

BACKGROUND

The present disclosure relates generally to object or surface treatment systems and methods and, more particularly, to a disinfecting and/or drying system for objects, containers, manufacturing assemblies, or structural surfaces.

A variety of systems transfer air or other fluids from a fluid supply source to one or more fluid discharge devices. In some systems, an arrangement of fluid conduits, which may include metal pipes, plastic pipes, and/or hoses, may provide a flow path for routing, channeling, or otherwise delivering a fluid from a fluid supply source to a fluid discharge device, such as an air manifold. Air received via an inlet may be directed through one or more fluid conduits or manifolds, and applied to a container via a series of nozzles. The output of the nozzles may be used for a variety of applications, such as drying and removing moisture from objects, removing dust or debris, cooling, surface preparation, and so forth. In some systems, particles, including germs and pathogens, may exist on containers or other surfaces. Thus, a system to treat containers is desirable.

Limitations and disadvantages of conventional and traditional approaches will become apparent to one of skill in the art, through comparison of such systems with the present disclosure as set forth in the remainder of the present application with reference to the drawings.

BRIEF SUMMARY

Systems and methods for treating an object, in particular, for disinfecting and/or drying containers and/or conveyance assemblies are disclosed herein. In some examples, an air delivery system to dry objects or remove debris may be coupled with an electromagnetic emitter (e.g., a Far ultraviolet (UV) light tubes) and/or a gaseous hydrogen peroxide generator. The combined systems provide one or more of drying, blowing, air-rinsing, and disinfecting of the objects and/or surfaces concurrently.

Certain aspects of embodiments disclosed herein by way of example are summarized below. It should be understood that these aspects are presented merely to provide the reader with a brief summary of certain forms an invention disclosed and/or claimed herein might take, and that these aspects are not intended to limit the scope of any invention disclosed and/or claimed herein. Indeed, any invention disclosed and/or claimed herein may encompass a variety of aspects that may not be set forth below.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

The figures are not necessarily to scale. Where appropriate, the same or similar reference numerals are used in the figures to refer to similar or identical elements.

DETAILED DESCRIPTION

One or more specific embodiments will be described below. These described embodiments are provided only by way of example, and do not limit the scope of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is directed to systems and methods for treating an object, in particular, for disinfecting and/or drying containers and/or conveyance assemblies. One or more of an air delivery system, an electromagnetic emitter (e.g., a Far ultraviolet (UV) light source), and/or an air treatment device (e.g., a gaseous hydrogen-peroxide ($H_2O_2$) generator) may be used to condition ambient air to treat a surface or container for use (e.g., prior to filling the container, applying a surfactant, etc.).

In some examples, one or more of the air delivery system, electromagnetic emitter, and/or the air treatment device are employed concurrently. As a result, air (or other fluids) may be treated prior to transmission via the air delivery system, thereby applying disinfected air to a surface to implement drying, blowing, air-rinsing, etc., of a container or other surface. In some examples, the treated air is itself a disinfectant, degrading and/or neutralizing contaminants. In some examples, one or more treatments are applied directly to the container or surface (e.g., direct exposure to Far UV light).

Air drying systems are widely used in preparation of food or beverage containers, such as cans or bottles, and may be used for pharmaceutical packaging preparations. In some examples, air drying systems are used for removing dust and other debris from sensitive products, such as printed circuit boards (PCBs). In addition, some embodiments of the system may also utilize air flow to disinfect the conveyance assembly. In some examples, an ionizer may be employed to charge particles in the ambient air to eliminate static that causes dirt, debris, or other contaminants to adhere to surfaces.

Many packaging surfaces and areas where packages are being prepared and/or filled may be exposed to contaminants that may be harmful to individual health. Contaminants may include one or more of bacterial (e.g., *Streptococcus, Pseudomonas*, MRSA, *Staphylococcus aureus*), fungal (*Aspergillus*) and viral (SARS-CoV-2, smallpox, influenza, mumps, measles, chickenpox, Ebola, HIV, and rubella) pathogens, among others, which may pose potential health risks due to ease of transmission and robustness of the contaminates in a variety of environmental conditions.

Accordingly, surfaces of containers and/or preparation areas should be disinfected prior to filling. Disinfecting such objects may minimize the spread, or the risk of spread, of disease or other contaminants.

Advantageously, the disclosed treatment system eliminates the need to apply disinfecting chemicals (which may require washing and/or can leave a harmful residue), or ozonated water, among other undesirable treatments. Further the disclosed treatment system is capable of disinfecting internal and external surfaces of a container.

In some examples, Far UV light is applied to disinfect objects. Advantageously, Far UV light does not carry the personnel hazards associated with other electromagnetic spectrums (e.g., UV-C), while providing robust disinfecting properties. For example, Far UV operates in a range of wavelengths between approximately 200 nm and 240 nm, below the UV-C energy levels. Thus, exposure to skin and eyes does not carry the same safety concerns, as it does not penetrate the skin or retinal cornea, as UV-C light would.

In disclosed examples, a system for disinfecting an object is provided. The system includes a Far ultraviolet (UV) emitter to degrade one or more contaminants on a surface of the object. An air delivery system is provided and configured to ingest ambient air, direct the ambient air through one or more conduits to force air to dry and blow debris from the surface of the object In some examples, the Far UV emitter is further configured to apply Far UV light directly to the object. In some examples, an ionizer charges particles in the ambient air.

In some examples, a housing integrates one or more of the Far UV emitter, the ionizer, and the air delivery system. In examples, the housing is a manifold to receive and contain the ambient air for treatment by the ionizer.

In some examples, an enclosure contains one or more of the housing, the Far UV emitter, the ionizer, the air delivery system, the object, and the treated air during a disinfecting operation.

In some examples, an exhaust system to remove treated air from a treatment area following a disinfecting operation. In some examples, one of a position or an orientation of the Far UV emitter is adjustable.

In disclosed examples, a system for disinfecting an environment is provided. The system includes a gaseous hydrogen peroxide generator, an air delivery system configured to ingest ambient air, direct the ambient air through the gaseous hydrogen peroxide generator, wherein the gaseous hydrogen peroxide generator converts hydrogen and oxygen molecules in the ambient air into gaseous hydrogen peroxide, and apply the treated air to the environment to be disinfected.

In some examples, an ionizer charges particles in the ambient air.

In some examples, control circuitry configured receives one or more user inputs to control the ionizer, the gaseous hydrogen peroxide generator, the air delivery system, or a conveyance assembly during a disinfecting operation.

When introducing elements of various embodiments described below, the articles "a," "an," and "the" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed subject matter, it will be appreciated that these examples are illustrative in nature and that the term "exemplary" is not used herein to denote any preference or requirement with respect to a disclosed aspect or embodiment. Additionally, it should be understood that references to "one embodiment," "an embodiment," "some embodiments," and the like are not intended to be interpreted as excluding the existence of additional embodiments that also incorporate the disclosed features.

As used herein, the terms "first" and "second" may be used to enumerate different components or elements of the same type, and do not necessarily imply any particular order.

As used herein, the terms "coupled," "coupled to," and "coupled with," each mean a structural and/or electrical connection, whether attached, affixed, connected, joined, fastened, linked, and/or otherwise secured. As used herein, the term "attach" means to affix, couple, connect, join, fasten, link, and/or otherwise secure. As used herein, the term "connect" means to attach, affix, couple, join, fasten, link, and/or otherwise secure.

As used herein the terms "circuits" and "circuitry" refer to any analog and/or digital components, power and/or control elements, such as a microprocessor, digital signal processor (DSP), software, and the like, discrete and/or integrated components, or portions and/or combinations thereof, including physical electronic components (i.e., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, circuitry is "operable" and/or "configured" to perform a function whenever the circuitry comprises the necessary hardware and/or code (if any is necessary) to perform the function, regardless of whether performance of the function is disabled or enabled (e.g., by a user-configurable setting, factory trim, etc.).

The terms "control circuit," "control circuitry," and/or "controller," as used herein, may include digital and/or analog circuitry, discrete and/or integrated circuitry, microprocessors, digital signal processors (DSPs), and/or other logic circuitry, and/or associated software, hardware, and/or firmware. Control circuits or control circuitry may be located on one or more circuit boards that form part or all of a controller, and are used to control a welding process, a device such as a power source or wire feeder, and/or any other type of welding-related system.

Figure 1A:
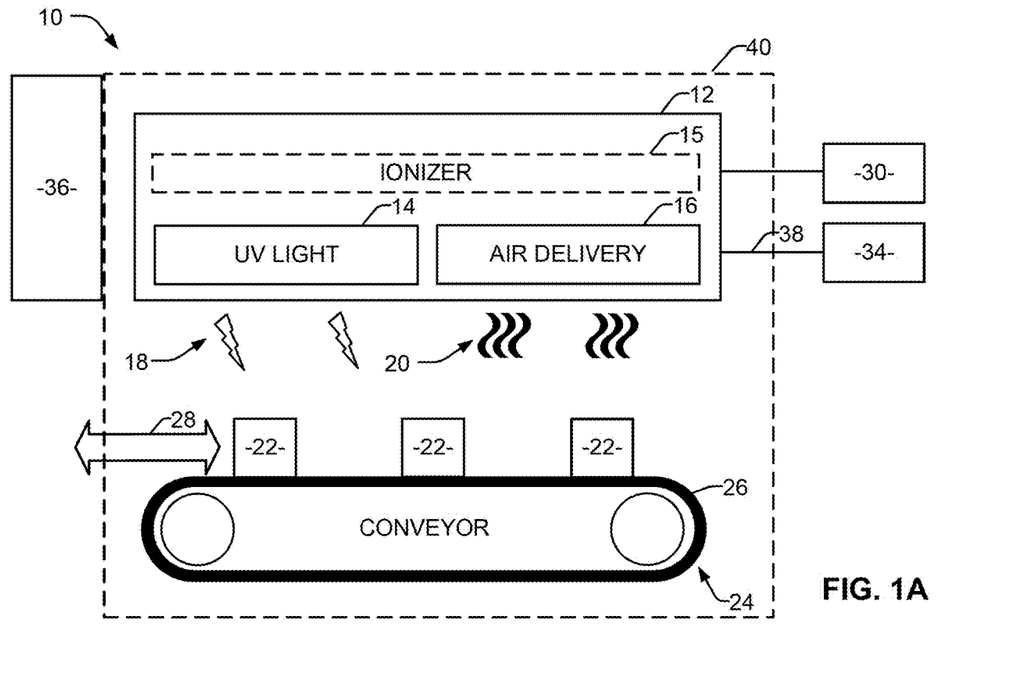
FIGS. 1A and 1B illustrate block diagrams depicting example treatment systems including one or more treatment devices, in accordance with the present disclosure.

Turning now to the drawings, FIG. 1A illustrates a treatment system 10 for an object 22 that may incorporate one or more disinfecting or treatment devices. Example treatment devices include an electromagnetic emitter 14 (e.g., a Far UV light source) and/or a ionizer 15. For example, the emitter 14 and/or the ionizer 15 may be employed to treat air from an air supply 34 (e.g., contained air and/or environmental/ambient air), which is delivered to air deliver system 16 via conduits 38 (e.g., a flexible hose, a pipe, a duct, a plenum, etc.). As disclosed herein, the one or more treatment devices may be coupled with or incorporated within a manifold, plenum, ductwork, or other volume of the air delivery system 16 to disinfect the air for a variety of functions including, but not limited to, drying products, removing dust or debris, coating control, cooling, leak detection, surface impregnation, corrosion prevention, and so forth. In some examples, the treatment devices are employed to disinfect containers and/or surfaces directly.

In some examples, the emitter 14, and/or the air delivery system 16, are arranged within a housing 12, which may also serve as a manifold for air treatment. In some examples, the air delivery system 16 extends from the housing 12 and/or the blower 34. The air delivery system 16 provides air flow paths to any number of outlets, such as additional air manifolds, air knives, flow dividers, etc.

In some examples, the air supply 34 includes a blower to force air to or through the housing 12 and/or the air delivery system 16 (through one or more ducts, conduits). Such a blower provides air flow at a relatively low pressure, yet with relatively high flow rates ducted to air delivery device to contact and treat an object, surface, conveyor assembly, etc. In disclosed examples, any number and/or configuration of air outlets may output air as a curtain of air (e.g., via an air knife) and/or directed or focused air (e.g., via nozzles). For instance, an example air knife may be fed by high pressure air from a pressurized air source (e.g., at a range of 80 to 100 psi), where the high pressure air mixes with ambient air upon exiting the air delivery device, such that a high volume of low pressure air comes into contact with a surface of the object, system, environment, etc., at a relatively low velocity.

Figure 1B:
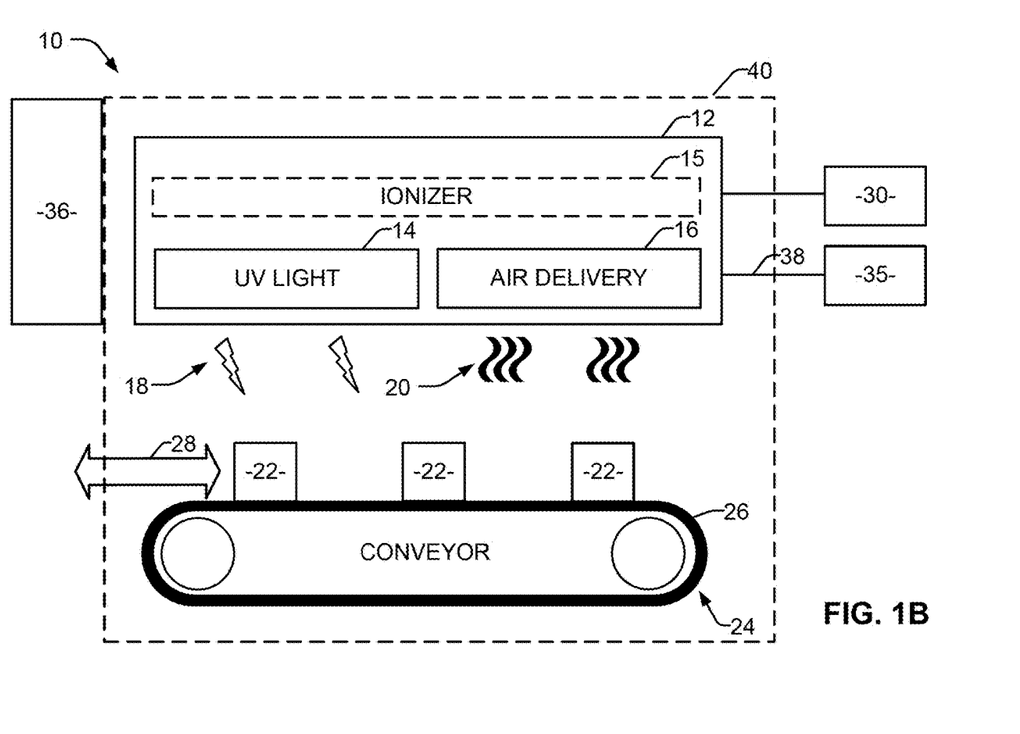

As shown in FIGS. 1A and 1B, an ionizer 15 may be additionally or alternatively provided (such as an ionizing bar or emitter), which can be paired with the air delivery system 16 (e.g., air knives, air manifolds, ducting, nozzles, etc.) and/or the Far UV emitter 14. The resulting ionization of the air partially or completely eliminates static that causes dirt, debris, or other contaminants to adhere to surfaces of the object, system, or environment to be treated.

Although illustrated as arranged above the conveyance assembly 24, the housing 12 and/or devices 14 or 16 may be located beneath, on a side, and/or at various angles and/or at various numbers within the treatment area. For instance, the geometry and placement of objects or surfaces may require Far UV light be directed from a particular angle along the conveyor belt 26 to ensure a desired surface is disinfected (e.g., an interior of a container). The arrangement and/or angle of each device may be adjustable, either by automatic means (e.g., a robotic system), and/or manually.

In operation, the objects 22 may be arranged on a belt or other moveable surface 26 of the conveyance assembly 24 to present the objects 22 to an output of the treatment devices. For example, objects 22 traverse the area below the housing 12 in direction 28, and are thereby exposed to far UV light 18 and treated air 20, having a disinfecting effect on the objects 22 and their immediate environment.

For example, the treatment area may be contained within an optional enclosure 40. Enclosing the treatment devices and/or the treatment are within the enclosure 40 (e.g., by one or more curtains, shields, walls, or other type of cover) provides a controlled environment in which to condition the objects therein, without needlessly exposing the surroundings or personnel to light 18 or conditioned air 20. In some examples, an exhaust system 36 is coupled to the system 10 to evacuate air or other fluids, as well as dust, debris, or other contaminants, from the treatment area following disinfecting of the objects 22 or conveyance assembly 24.

The devices may be powered and/or controlled by a power source 30, which may include a user interface, a processor, a memory, a network interface, one or more power conversion circuits, or other circuits to power and/or control the system 10. The power source 30 may have an integrated computed platform or be connected to a remote system from which it can receive commands, including a coordinated routine for operating the treatment devices and the conveyance assembly 24. For example, operations may be optimized based on a variety of factors. For instance, operating parameters such as conveyance speed, number and intensity of Far UV emitters, and whether to activate the ionizer 15, as a list of non-limiting examples, may depend on one or more variables, such as a type of surface material for disinfecting, a geometry of the surface to be disinfected, and a desired level of disinfecting (e.g., for food grade packaging, medicinal items, or less sensitive items), as a list of non-limiting examples. Thus, inputting one or more variables into the power source 30 may automatically determine one or more operating parameters, which are used for coordinated operation of the treatment devices and conveyance assembly.

Although some example electromagnetic emitters are described as outputting light in the far UV range, other electromagnetic outputs may be employed. Additionally or alternatively, light in the UV-C range and/or one or more laser lights may be used as a disinfectant, in accordance with the concepts disclosed herein. In some examples, an electrostatic tool can be substituted for another treatment device, and/or added as an additional disinfectant.

FIG. 1B illustrates another example system 10 with an air compressor 35 (and/or air amplifier) to provide pressurized air to or through the housing 12 and/or the air delivery system 16. For instance, an output of the air delivery system 16 may be directed to a surface via a nozzle. In disclosed examples, any number and/or configuration of air outlets may output directed or focused air (e.g., via nozzles). For instance, an example air nozzle may receive high pressure air from a pressurized air source (e.g., at a range of 80 to 100 psi), where the high pressure air mixes with ambient air upon exiting the air delivery device, such that a high volume of low pressure air comes into contact with a surface of the object, system, environment, etc.

Figures 2A, 2B:
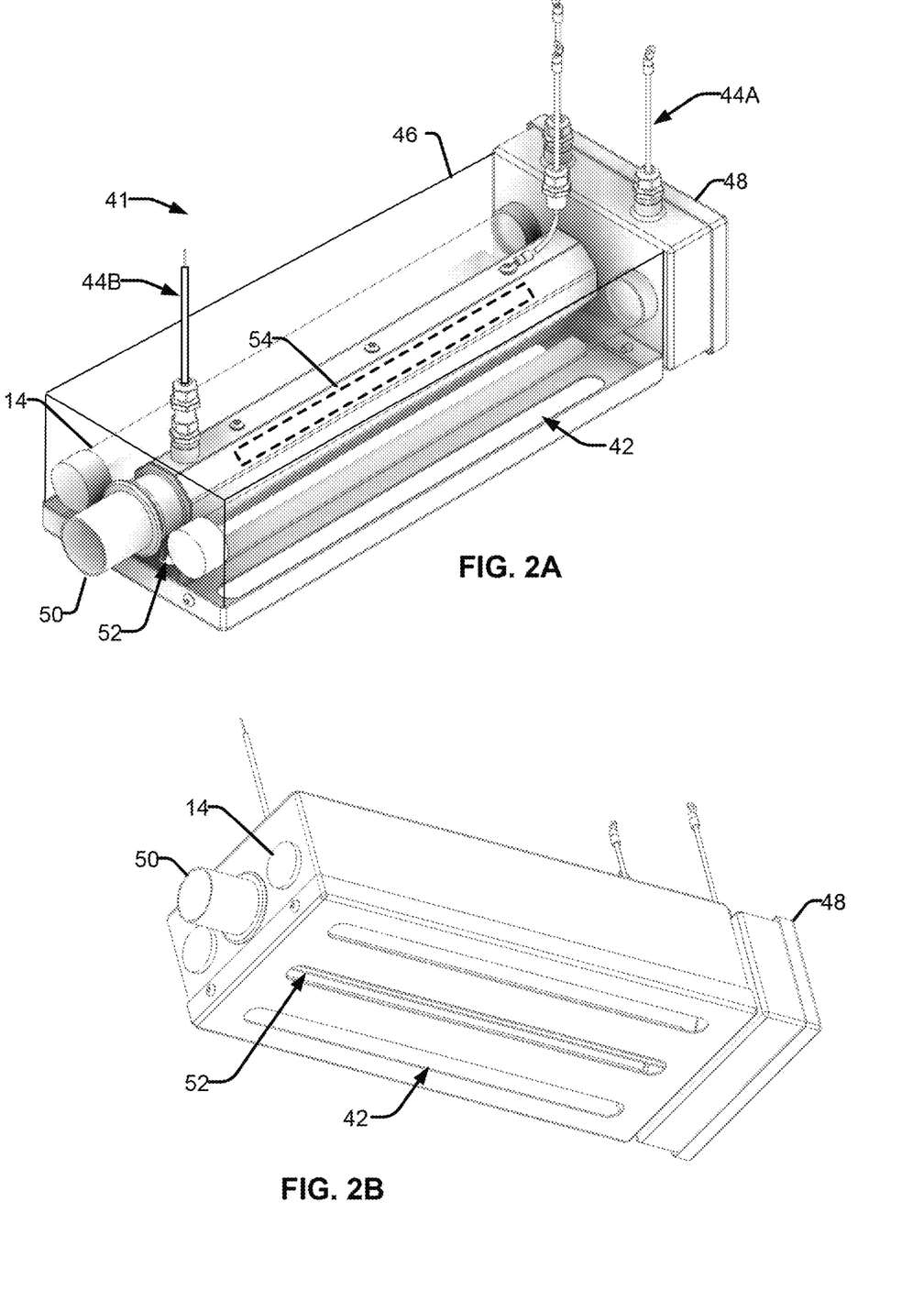
FIGS. 2A and 2B illustrate perspective views of an example treatment device of FIG. 1.

In the examples illustrated in FIGS. 2A and 2B, one or more far UV light emitters 14 (e.g., light emitting tubes) are provided as one or more separate tubes, secured within a package 41 and/or other fixed structure associated with the treatment system 10. In some examples, one or more containers 41 of Far UV light emitters 14 are arranged within the enclosure 40 and/or the treatment area. The orientation of the package 41 may be configured to change (e.g., automatically and/or manually) relative to the containers to perform a disinfecting operation. In some examples, a single Far UV light emitters 14 may be employed, configured to move during an operation to disinfect multiple containers, surfaces, or different components of the system 10.

As shown in FIGS. 2A and 2B, a cover 46 may enclose or protect the emitter tubes, light from which may be directed outward via one or more windows 42 arranged within a package 41 to control operation of the emitters 14 and direct Far UV light (and/or conditioned air) toward the treatment area. The windows 42 may be dimensioned to focus the light to a desired area or object, and may be moveable (e.g., to an open, a closed, or a partially open position).

Conductor 44A may provide power and/or control signals from the power source 30 to a dedicated power supply 48 configured to distribute power and coordinate control of the emitters 14 (and/or the windows 42) with the other components of the system 10.

As shown in FIGS. 2A and 2B, the ionizer 15 is provided as an ionizing bar 54 arranged within an air delivery duct or conduit 50, which is configured to output air via an air knife 52. In some examples, the ionizing bar 54 is internal to an air manifold or other conduit, duct, etc. Conductor 44B may provide power and/or control signals from the power source 30 to the ionizing bar 54.

Although illustrated as being incorporated within a conduit 50 feeding the air knife 52, in some examples the ionizing bar 54 may be arranged external to a conduit feeding the air output. These and other arrangements of ionizers (relative to a Far UV emitter, air delivery system, and/or the $H_2O_2$ generator of FIGS. 3A and 3B) may be employed in systems 10 with a blower, air compressor, and/or other air sources for treatment of an object or surface.

Figure 3A:
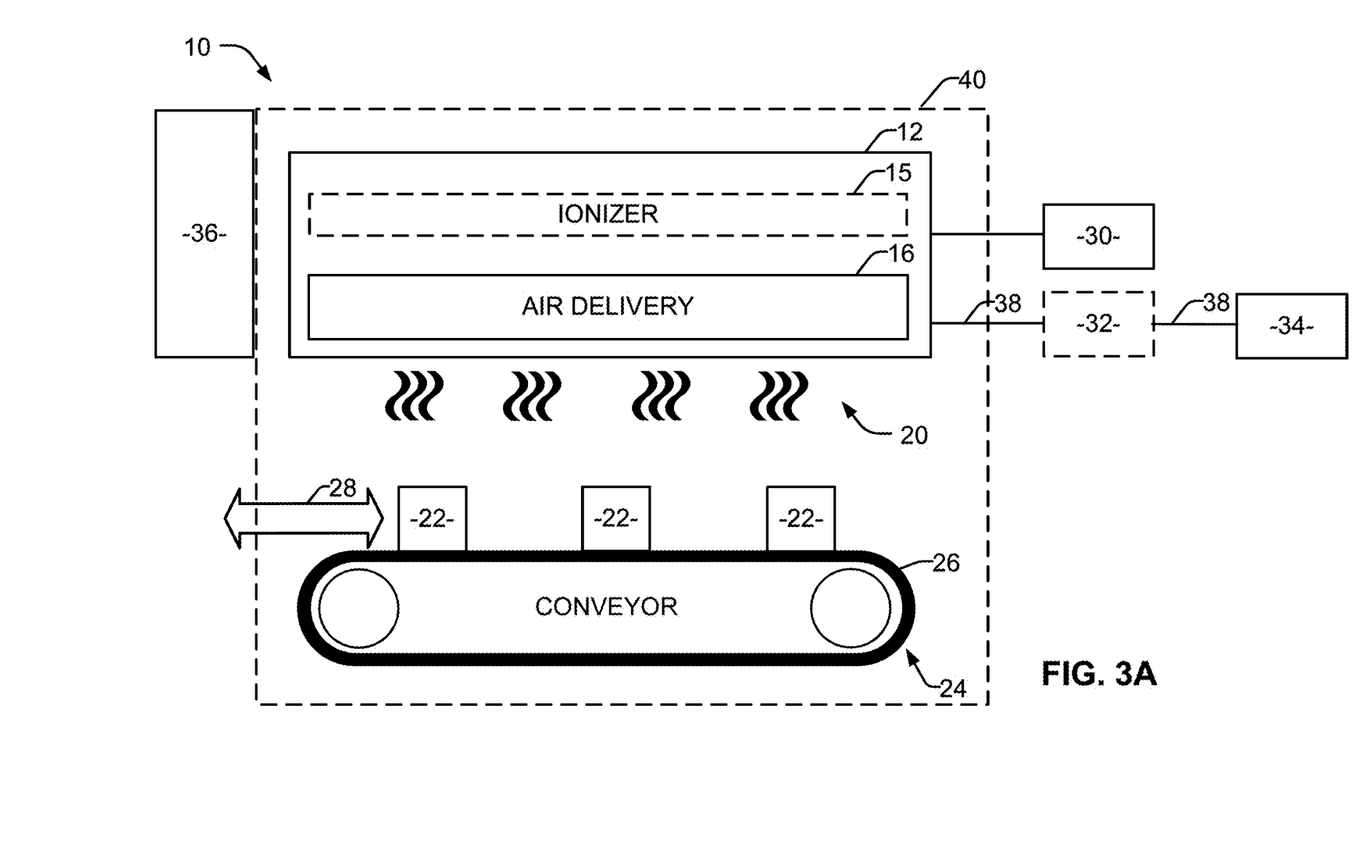
FIGS. 3A and 3B illustrate block diagrams depicting other example treatment systems including one or more treatment devices, in accordance with the present disclosure.

Turning to FIG. 3A, an additional or alternative treatment system 10 for an object 22 (or system or environment) is provided incorporating one or more disinfecting or treatment devices. For example, treatment devices may include a gaseous hydrogen peroxide ($H_2O_2$) generator 32, which may be employed to treat air from an air supply 34 (e.g., contained air and/or environmental air), the treated air then being delivered to the air delivery system 16 via conduits 38 (e.g., a flexible hose, a pipe, etc.). As disclosed herein, the one or more treatment devices may be coupled with an air delivery system 16 to disinfect the air (and/or other surface) for a variety of functions including, but not limited to, drying products, removing dust or debris, coating control, cooling, leak detection, surface impregnation, corrosion prevention, and so forth.

In some examples, the $H_2O_2$ generator 32 is arranged within housing 12 (e.g., a duct or manifold for air treatment). In additional or alternative examples, the $H_2O_2$ generator 32 is arranged at the air supply 34, within the housing 12, and/or at any point along the conduits 38. The $H_2O_2$ generator 32 may be configured to ingest ambient air, filter and treat the ambient oxygen to create a gaseous $H_2O_2$, which can serve as a disinfectant in the ambient environment, including the air and surfaces of the objects 22 or conveyance assembly 24.

In some examples, one or more air delivery system 16 is coupled to the housing 12, the blower 16, and/or the $H_2O_2$ generator 32. The conduits or other outlets provide air flow paths to any number of objects or surfaces, such as additional air manifolds, air knives, flow dividers, etc. Further, although illustrated as a single unit, two or more $H_2O_2$ generators 32 may be employed, arranged along various points in the air flow paths, including treatment of air previously treated by another $H_2O_2$ generator 32. For instance, concentrations of $H_2O_2$ in the treated air may enhance a disinfecting operation. Thus, treating the air at a shorter distance to the surface to be treated and/or increasing a concentration of $H_2O_2$ in the air may increase disinfecting effectiveness. Modifications to the concentration of $H_2O_2$ in the air may call for certain precautions to be put in place, such as employing or enhancing enclosure 40 or exhaust 36, as a list of non-limiting examples.

Although illustrated as arranged above the conveyance assembly 24, the housing 12 and/or treatment devices 15 or air delivery systems 16 may be located beneath, on a side, and/or at various angles and/or at various numbers within the treatment area. For instance, the geometry and placement of objects or surfaces may require air flow to be directed from a particular angle along the conveyor belt 26 to ensure a desired surface is disinfected (e.g., an interior of a container). The arrangement and/or angle of each device may be adjustable, either by automatic means (e.g., a robotic system), and/or manually.

Similar to the system 10 of FIGS. 1A and 1B, the devices including the $H_2O_2$ generator 32 may be powered and/or controlled by a power source 30, which may include a user interface, a processor, a memory, a network interface, one or more power conversion circuits, or other circuits to power and/or control the system 10. The power source 30 may have an integrated computed platform or be connected to a remote system from which it can receive commands, including a coordinated routine for operating the treatment devices and the conveyance assembly 24. For example, operations may be optimized based on a variety of factors. For instance, operating parameters such as conveyance speed, and volume of air to be treated, as a list of non-limiting examples, may depend on one or more variables, such as a type of surface material for disinfecting, a geometry of the surface to be disinfected, and a desired level of disinfecting (e.g., for food grade packaging, medicinal items, or less sensitive items), as a list of non-limiting examples. Thus, inputting one or more variables into the power source 30 may automatically determine one or more operating parameters, which are used for coordinated operation of the treatment devices and conveyance assembly.

Figure 3B:
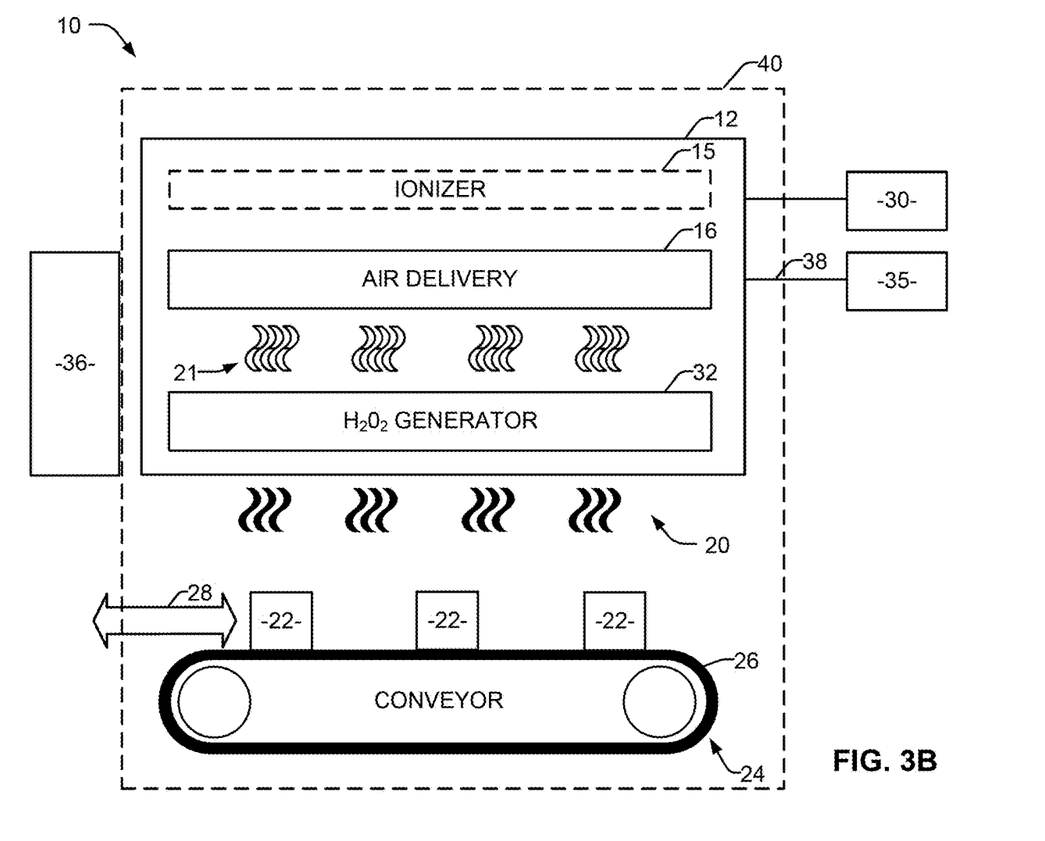

Turning to FIG. 3B, a source of compressed air 35, such as an air compressor, may be employed to increase the pressure of air provided to the air delivery system 16. For example, the air compressor 35 may force air through conduit 38 into the air delivery system 16 (e.g., a manifold, air knife, nozzle, etc.), as pressurized, untreated air 21. The untreated air 21 is then provided to an $H_2O_2$ generator 32 arranged downstream from the air delivery system 16, creating treated air 20 directed toward the objects 22 to be treated.

The systems disclosed herein are applicable to any number of disinfecting, sanitizing, and/or cleaning techniques or tasks not specifically provided in the illustrated or described examples. For example, clean room environments, systems, and/or operations may be treated employing one or more of the treatment devices disclosed herein. In such an example, a blower (e.g., electric, pneumatic, etc.) may be housed or otherwise contained or coupled with an ionizer, Far UV emitter, and/or $H_2O_2$ generator, and output a light and/or treated/ionized air into a clean room environment. Such a system may be arranged in a ceiling mounted unit, or otherwise located and/or oriented for specific treatment outcomes.

While only certain features of the invention have been illustrated and described herein, many modifications and changes will occur to those skilled in the art. It is, therefore, to be understood that the appended claims are intended to cover all such modifications and changes as fall within the true spirit of the invention.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

As used herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

As utilized herein, the terms "e.g.," and "for example" set off lists of one or more non-limiting examples, instances, or illustrations.

What is claimed is:

1. A system for disinfecting an object comprising:
a Far ultraviolet (UV) emitter to degrade one or more contaminants on a surface of the object; and
an air delivery system configured to:
ingest ambient air; and
direct the ambient air through one or more conduits to force air to dry and blow debris from the surface of the object.

2. The system of claim 1, wherein the ambient air is treated by Far UV light from the Far UV emitter prior to being directed through the one or more conduits.

3. The system of claim 1, wherein the Far UV emitter is further configured to apply Far UV light directly to the object.

4. The system of claim 1, further comprising an ionizer to charge particles in the ambient air.

5. The system of claim 4, further comprising a housing to integrate one or more of the Far UV emitter, the ionizer, and the air delivery system.

6. The system of claim 5, wherein the housing is a manifold to receive and contain the ambient air for treatment by the ionizer.

7. The system of claim 5, further comprising an enclosure to contain one or more of the housing, the Far UV emitter, the ionizer, the air delivery system, the object, and the treated air during a disinfecting operation.

8. The system of claim 1, further comprising an exhaust system to remove treated air from a treatment area following a disinfecting operation.

9. The system of claim 1, wherein one of a position or an orientation of the Far UV emitter is adjustable.

10. A system for disinfecting an object comprising:
a Far ultraviolet (UV) emitter to degrade one or more contaminants on a surface of the object;
an ionizer to charge particles in ambient air; and
an air delivery system configured to:
ingest ambient air; and
direct the ambient air across the ionizer or through one or more conduits to force air to dry and blow debris from the surface of the object.

11. The system of claim 10, wherein the air delivery system comprises an air delivery conduit to channel the ambient air toward the object.

12. The system of claim 11, wherein the ionizer comprises an ionizing bar arranged within and extending through a portion of the air delivery conduit.

13. The system of claim 12, wherein the air delivery conduit is configured to direct the ambient air across a portion of the ionizing bar and output the ambient air via an air knife.

14. The system of claim 11, wherein the air delivery conduit comprises one or more of an air manifold or duct.

15. The system of claim 10, wherein the ionizer comprises an ionizing bar arranged external to a conduit feeding the ambient air toward the object.

16. The system of claim 10, wherein the air delivery system comprises a cover to enclose one or more of the Far UV emitter or the ionizer.

17. The system of claim 16, wherein the cover comprises one or more windows arranged to direct Far UV light or conditioned air from the air delivery system toward the object within a treatment area.

18. The system of claim 17, wherein the one or more windows are manually or mechanically moveable to an open, a closed, or a partially open position.

19. The system of claim 10, further comprising a gaseous hydrogen peroxide generator.

20. The system of claim 19, wherein the air delivery system is further configured to direct the ambient air through the gaseous hydrogen peroxide generator, wherein the gaseous hydrogen peroxide generator converts hydrogen and oxygen molecules in the ambient air into gaseous hydrogen peroxide.

* * * * *